United States Patent [19]

Spector et al.

[11] 4,424,833

[45] Jan. 10, 1984

[54] SELF SEALING GASKET ASSEMBLY

[75] Inventors: Kenneth A. Spector, Framingham, Mass.; Wilfred Samson, Santa Clara, Calif.; Richard M. DeMello, Falmouth, Mass.

[73] Assignee: C. R. Bard, Inc., Murray Hill, N.J.

[21] Appl. No.: 307,888

[22] Filed: Oct. 2, 1981

[51] Int. Cl.³ .................. A61M 5/00; A61M 25/00
[52] U.S. Cl. ............................ 137/849; 128/202.15; 277/165; 604/167
[58] Field of Search .................. 277/165; 128/202.15, 128/656, 658, 763, 768; 604/167, 164, 43, 280; 137/849

[56] References Cited

U.S. PATENT DOCUMENTS

| 584,091 | 6/1897 | Leidich | 137/849 |
| 2,023,267 | 12/1935 | De Saint Rapt | 128/202.15 |
| 3,097,646 | 7/1963 | Scislowicz | 604/167 |
| 3,459,183 | 8/1969 | Ring et al. | 128/763 |
| 4,311,137 | 1/1982 | Gerard | 604/167 |

FOREIGN PATENT DOCUMENTS 670683 9/1963 Canada ........................ 128/202.15

Primary Examiner—Robert I. Smith
Attorney, Agent, or Firm—Wolf, Greenfield & Sacks

[57] ABSTRACT

A molded one-piece, self-sealing gasket maintains its seal at all times including during insertion of a tube, such as a catheter, as well as after the tube is withdrawn.

8 Claims, 4 Drawing Figures

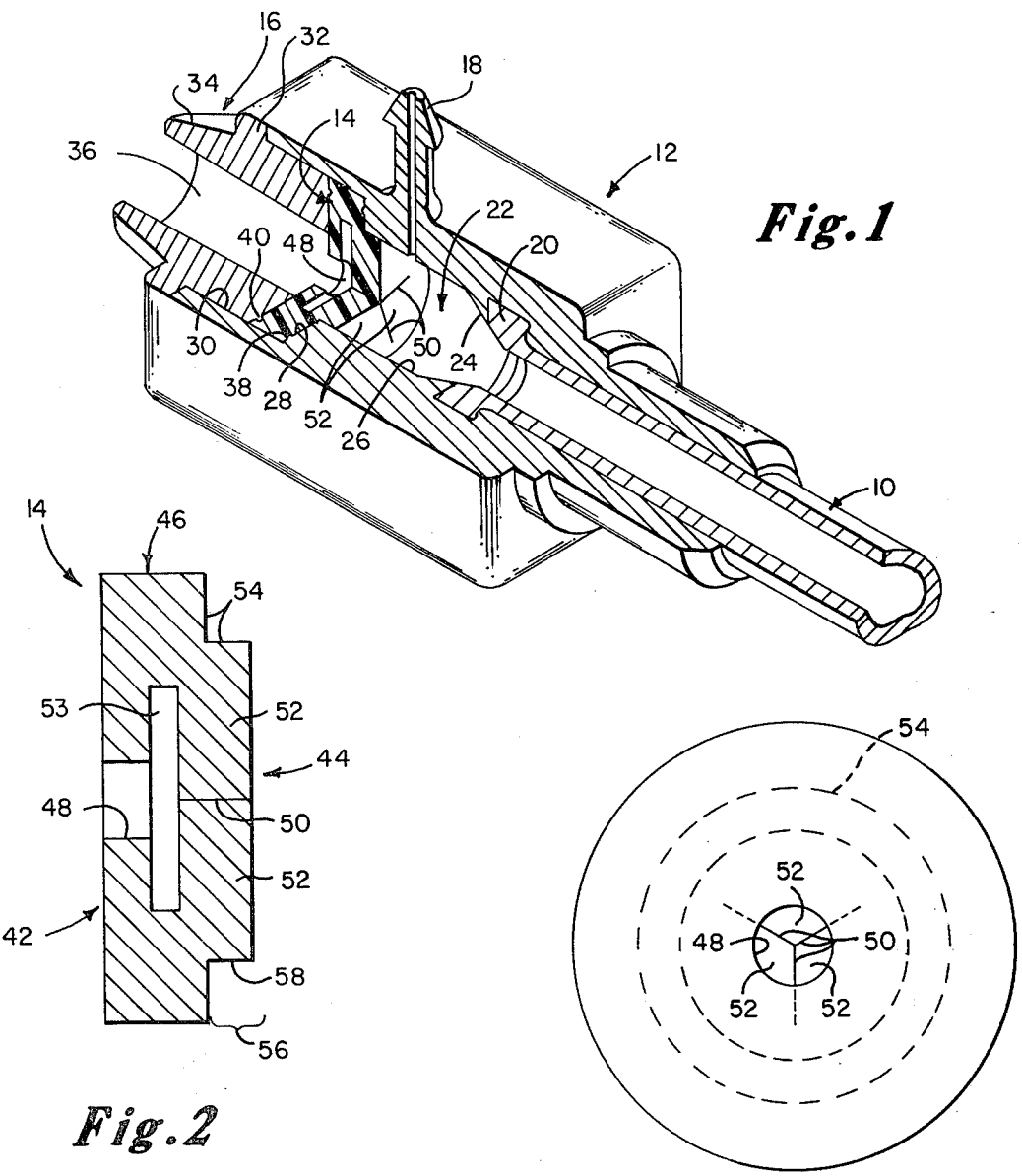
*Fig.1*
*Fig.2*
*Fig.3*
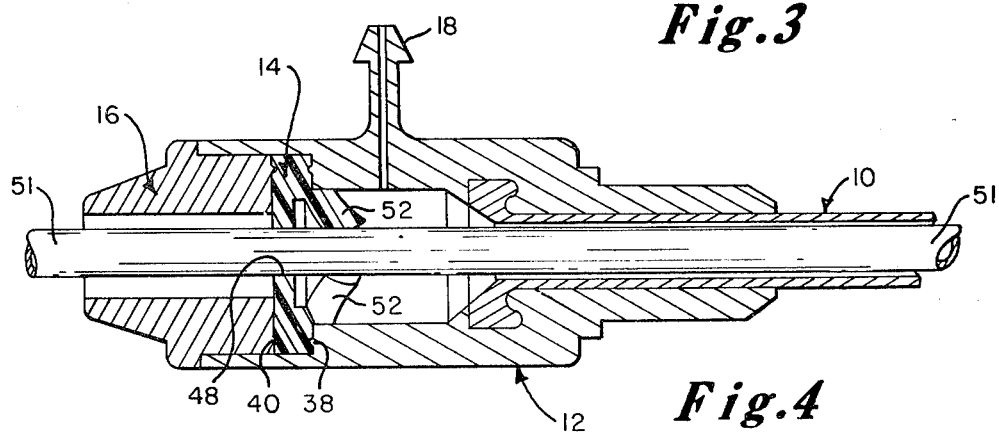
*Fig.4*

SELF SEALING GASKET ASSEMBLY

BACKGROUND OF THE INVENTION

This invention relates to improvements in self-sealing gaskets, particularly valve-like gaskets through which tubes may be inserted and removed, and in which the valve-gasket maintains a seal at all times. Devices of this type are used in a variety of environments, such as medical environments, in which it is often required to insert one tube through another tube or into a housing or vessel while maintaining the outer tube, housing or vessel sealed at all times. Other environments in which such devices have been used include gas masks or sealed helmets, to provide a self-sealing valve through which a feeding tube or the like may be inserted and withdrawn repeatedly, while maintaining a seal at all times. For example, U.S. Pat. No. 2,023,267 to DeSaint Rapt illustrates a gas mask having a self-sealing valve formed of a plurality of apertured and slitted disks arranged face-to-face through which a feeding tube may be inserted or withdrawn. Similarly, U.S. Pat. No. 3,067,425 to Colley illustrates a modified form of self-sealing device in an aviator's helmet having a different configuration of slits and apertures in the various face-to-face disks.

U.S. Pat. No. 4,000,739 to Stevens illustrates an analogous use for such a self-sealing gasket arrangement in a catheter introducer. The catheter introducer illustrated in the Stevens patent includes a tube which is intended to be inserted into and which remains in place in a patient's blood vessel. A fitting on the externally projecting end of the tube is provided with a self-sealing gasketing device to enable catheters to be introduced into the patient's blood vessel through the self-sealing introducer. The catheter introducer may remain in place in the patient's blood vessel for a period of time during which the various catheters may be inserted and withdrawn as may be determined by the particular medical procedure(s) at hand. Also illustrative of the medical environments where self-sealing valves or plugs may be used are shown in Ring U.S. Pat. No. 3,459,183 and Scislowicz U.S. Pat. No. 3,097,646 which show needles or other similar tubular introducer devices are placed in a blood vessel and in which the devices are provided with self-sealing plugs or the like on their outer ends to provide self-sealing access to the blood vessel.

When such a self-sealing device is used in a catheter introducer, it often may be desirable to provide a side entry port through which liquids may be introduced or through which the device may be aspirated (i.e. to withdraw blood or otherwise apply suction as desired). Thus, it is important that the self-sealing valve or plug maintain its seal over a relatively wide range of pressures to include not only the normal positive pressure of the patient's blood pressure but also the reduced pressure which results from aspiration through the side port. Also among the desirable features of a self-sealing device is that the seal should not unduly inhibit axial and rotary movement of a catheter through the seal.

The type of self-sealing device as illustrated in the Stevens, DeSaint Rapt and Colley patents is not without its difficulties. That type of device utilizes a number of slitted and apertured gasket disks in face-to-face relation. In each of these, it is necessary to manufacture a number of separate disks and to assemble them in a predetermined sequence and array, all of which adds to manufacturing costs. In addition, when used as a self-sealing cannula (as in the Stevens device) it has been found that while such multiple gasket devices are not wholly without difficulties. For example, the commercially available version of the device disclosed in the Stevens patent may not perform as well during aspiration as might be desired and in some instances, there is some risk that aspiration may ingest air into the system through the disks. It is believed that this is in part due to the use of two thin face-to-face gaskets which typify the Stevens construction.

It is among the general objects of the invention to provide an improved self-sealing gasket configuration for use in catheter introducers and the like.

SUMMARY OF THE INVENTION

In brief, the self-sealing gasket is molded in a single piece from a resilient material, such as latex rubber, to have an outer sealing portion and an inner sealing portion. The inner and outer sealing portions are joined by an integral peripheral side wall. The outer sealing segment has a central hole which forms a seal about the catheter or like tube when the tube is inserted through the device. The inner sealing segment includes a slotted member which defines a number of flaps. The flaps which remain in their normal closed configuration in the absence of a tube, spread apart upon the introduction of a catheter or like tube. When the catheter is withdrawn, the flaps return to their normal closed and self-sealing configuration. The one-piece molded self-sealing gasket is contained within a specially formed cavity which cooperates with the outer peripheral contour of the gasket to provide superior sealing both in a static pressure and aspiration mode, and whether the catheter is in place or not.

In the illustrative embodiment of the invention, the one-piece self-sealing member is contained within a housing attached to the end of an introducer tube. The housing has a hollow interior with a specially-formed shoulder surface to receive the self-sealing member. The self-sealing member is held in place by an end cap which is secured to the housing. A side port preferably is formed integrally with the housing to enable liquids to be introduced to the patient, or to facilitate blood pressure readings or for aspiration, or the like.

It is among the general objects of the invention to provide an improved self-sealing gasket.

A further object of the invention is to provide an improved catheter introducer or like device having a self-sealing gasket.

Another object of the invention is to provide a self-sealing device of the type described which provides superior sealing yet which does not adversely increase the resistance to manipulation of the catheter or other tube extending through the seal.

Another object of the invention is to provide a self-sealing device of the type described which is molded in a single integral piece and which results in economies and efficiencies in manufacture of the seal as well as in assembly of the seal into a receptive housing.

DESCRIPTION OF THE DRAWINGS

The foregoing and other objects and advantages of the invention will be appreciated more fully from the following further description thereof, with reference to the accompanying drawings wherein:

FIG. 1 is an illustration of the invention as embodied in the housing of a catheter introducer, broken away and sectioned to illustrate the internal structure of the device;

FIG. 2 is an enlarged sectional illustration of the one-piece self-sealing valve element of the present invention;

FIG. 3 is an illustration of the self-sealing valve member as viewed from the left side of FIG. 2; and FIG. 4 is an illustration of the device with a tube extending through the self-sealing valve with the flaps separated.

DESCRIPTION OF THE ILLUSTRATIVE EMBODIMENT

FIG. 1 shows a catheter introducer which incorporates the present invention. The introducer includes an introducer tube 10 which is connected to and extends from a housing 12. The one-piece molded self-sealing gasket, indicated generally by reference character 14 is mounted in the valve housing 12 in a manner described in more detail below. The gasket 14 is retained firmly in place in the housing 12 by an end cap 16. The housing 12 preferably is provided with a side port 18.

The introducer tube 10 preferably is formed from fluorinated ethylene and is formed separately with an enlarged head portion 20. The housing 12 preferably is molded directly onto the headed end of the introducer tube 10 and is locked securely and integrally with the introducer tube 10 by engagement with the head portion 20. The housing 12 is formed with a hollow interior 22 which forms a forwardly-tapering configuration, indicated at 24, which merges smoothly with the tapering inlet end of the head portion 20 of the introducer tube 10. The side port 18 is molded integrally with the housing 12 to provide a means to communicate directly with the hollow interior 22 in the housing 12.

The hollow interior 22 of the housing 12 defines a cylindrical bore 26 which terminates in an enlarged diameter shoulder 28. The shoulder 28 terminates in an enlarged diameter outer bore 30 which receives the end cap 16. The end cap 16 has an inner portion dimensioned to fit snugly within the outer bore 30. The cap 16 includes an outer peripheral collar 32 which engages the outer end of the housing to determine and limit precisely the extent to which the inner end of the end cap 16 extends into the outer bore 30. The outer end of the end cap 16 may include an extension 34 and a tapered inlet opening 36 may be formed through the end cap. The inlet 36 is tapered to enable a conventional Luer connector to be attached, if desired.

As shown in FIG. 1, the self-sealing gasket 14 is retained between the end cap 16 and the shoulder 28 of the housing 12. The shoulder 28 preferably is provided with a circular ridge 38 and an identical ridge 40 is formed on the facing inner surface of the inner end of the end cap 16. When the end cap 16 is fully seated, as determined by engagement of the collar 32 with the end of the housing 12, the ridges 38, 40 engage and effect a firm grip on the gasket 14.

As illustrated in enlarged detail in FIGS. 2-4, the gasket member 14 may be considered has having an outer sealing portion 42 and a spaced inner sealing portion 44. The outer and inner seals 42, 44 are molded integrally in a single piece, with a surrounding, connective peripheral side wall 46. The outer seal 42 is provided with a central aperture 48, preferably a circular hole. The inner seal 44 is provided with a plurality of slits, 50 which are arranged radially from the center of the inner seal 44. The slits 50 define a plurality of flaps 52 which deflect inwardly as the catheter 51, tube or the like is inserted through the device, as suggested in FIG. 4. The resilient flaps 52 return to their normally closed and sealed configurations automatically when the tube is withdrawn.

When a catheter is in place, the primary seal is effected by the outer seal 42 on the outer surface of the catheter. When the catheter is withdrawn, the seal is effected by the closure of the flaps 52. The configuration of the valve 14 is such that the flaps 52 effect a full and complete self-seal independently and require no backing up, reinforcement or other support. The hole 48 and space 53 between the seals 42, 44 is of generally T-shaped cross section (FIG. 2). The inner seal 44 is of substantially greater thickness than the outer seal 42, at least in the more radially inwardly disposed portions. The inner seal 44 is formed to define a peripheral shoulder 54 which fits against the shoulder 28 of the housing 12. The more central portion of the inner seal 44 includes the thicker plug portion 56 which extends into and fits within the bore 26 of the housing 12. The outer periphery 58 of the plug portion 56 thus is confined and supported by the bore 26.

The thickness of the plug portion 56 on the inner seal 44 should be substantially equal to half of the total thickness of the valve 14. The circle diameter defined by the slits 50 is substantially equal to the inner diameter of the inner cylindrical space 53 in the valve 14.

In using the illustrative embodiment of the invention, the introducer tube 10 may be inserted into the patient's blood vessel by any of the various available surgical techniques for that purpose (e.g. percutaneous, cut down, etc.), as is desired by the particular physician. Once the introducer is properly placed, it may be taped down to the patient's skin or otherwise secured in place. From that point on, catheters may be introduced through the self-sealing gasket 14 of the housing 12 and catheter changes may be made as desired. When used in angiographic procedures or other surgical techniques in which the physician must be able to feel obstructions to the advancing catheter tip by feeling resistance at the proximal end of the catheter, the resistance offered by the valve 14 of the present invention is relatively insignificant and does not interfere with the surgeon's feel. The side port, of course, may be used in the manner in which side ports are normally used, for example, to infuse medicine, intravenous nourishment or to take blood pressure measurements. The side port may be aspirated to withdraw blood samples if desired. In the aspiration mode, the present invention has been found to provide superior sealing results.

It is believed that part of the reason for the improved sealing results of the present invention results from the increased thickness of the plug portion 56 of the rubber gasket 14 and the manner by which that plug portion is mounted to be constrained peripherally within the bore 26 of the housing 12. It is believed that the arrangement in which the flaps 52 hinge near the periphery of the plug portion and the additional support for the increased thickness of the plug portion 56 by the engagement of the shoulder 28, 54, are significant contributing factors to the advantages of the present invention.

As mentioned above, the gasket 14 provides a number of advantages not only in operation of the device but as well as in economies of the manufacture. The device is moldable from latex rubber or the like and can be formed in a relatively simple single-molding procedure.

During assembly of the introducer body, there is only a single valve element to be placed in the housing 12.

While the invention has been illustrated as being used in connection with a catheter introducer, it should be noted that it is not necessarily limited in scope to use in that sole environment and that the principle of the invention may be incorporated and utilized in other analogous environments and devices.

Thus, it should be understood that the foregoing descriptiion of the invention is intended merely to be illustrative thereof and that other modifications and embodiments of the invention may be apparent to those skilled in the art without departing from its spirit.

Having thus described the invention, what I desire to claim and secure by Letters Patent is:

1. A self-sealing gasket assembly to permit a tube to be inserted into or withdrawn from a housing while maintaining the interior of the housing under seal comprising:
   - a one-piece disc-shaped gasket having an outer sealing portion, an inner sealing portion and a peripheral sidewall portion connecting the inner and outer sealing portions, the inner, outer and sidewall portions being constructed and arranged so that the inner and outer sealing portions are spaced from each other;
   - an aperture formed in the outer sealing member;
   - means defining at least one slit in the inner sealing portion of the member;
   - the inner portion of the gasket having a shoulder formed about its periphery whereby the more central region of the inner sealing member defines an inwardly-extending central plug portion, said slit being formed within the plug portion;
   - a housing to receive the sealing member, the housing including an inner bore and an outer bore, the outer bore being larger than the inner bore and defining a shoulder at the juncture of the inner bore and the outer bore, the shoulder in the housing being constructed and arranged to receive the shoulder formed about the periphery of the inner sealing portion of the gasket and to peripherally constrain said plug portion thereby to provide support for said plug portion and the periphery of the gasket; and
   - means for securing the periphery of the gasket against the shoulder of the housing.

2. A device as defined in claim 1 further comprising: said aperture and said space between the inner and outer sealing members being substantially T-shaped in cross section.

3. A device as defined in claim 1 further comprising: the thickness of the rearwardly-facing sealing member being substantially equal to half of the total thickness of the gasket.

4. A device as defined in claim 3 further comprising: the thickness of said plug portion being less than the thickness of the inner sealing portion of the gasket.

5. A device as defined in claim 1 wherein the housing comprises a catheter introducer having an introducer sheath extending therefrom and a side port.

6. A device as defined in claim 5 wherein means for securing the gasket comprises a cap receivable within the outer bore of the housing and being adapted to lightly compress the periphery of the gasket member in the region circumscribing the plug.

7. A device as defined in claim 1 wherein the slot means includes a plurality of slots extending radially from the center of the plug portion, the slots defining a circle diameter substantially equal to the diameter of said space within the gasket.

8. A device as defined in claim 1 wherein the gasket is molded from latex rubber.

* * * * *